(12) United States Patent
Arce Johnson et al.

(10) Patent No.: US 7,994,397 B2
(45) Date of Patent: Aug. 9, 2011

(54) METHOD TO PRODUCE STERILE MALE FLOWERS AND PARTENOCARPIC FRUITS BY GENETIC SILENCING, ASSOCIATED SEQUENCES AND VECTORS CONTAINING SAID SEQUENCES

(75) Inventors: Jorge Patricio Arce Johnson, Santiago (CL); Maria Josefina Poupin Swinburn, Santiago (CL); Maria Consuelo Medina Arevalo, Santiago (CL); Agnes Cadavid Labrada, Santiago (CL); Fernán Federici Noe, Santiago (CL)

(73) Assignee: Pontificia Universidad Catolica de Chile, Santiago (CL)

( * ) Notice: Subject to any disclaimer, the term of this patent is extended or adjusted under 35 U.S.C. 154(b) by 517 days.

(21) Appl. No.: 11/948,397

(22) Filed: Nov. 30, 2007

(65) Prior Publication Data

US 2008/0216194 A1    Sep. 4, 2008

(30) Foreign Application Priority Data

Dec. 1, 2006    (CL) .................................. 3361-2006

(51) Int. Cl.
*C12N 15/29*    (2006.01)
*C12N 15/82*    (2006.01)
(52) U.S. Cl. ...................... 800/285; 800/287; 536/24.5
(58) Field of Classification Search .................... None
See application file for complete search history.

(56) References Cited

U.S. PATENT DOCUMENTS

2002/0010953 A1    1/2002 Vliet
2002/0152495 A1    10/2002 Ito et al.

FOREIGN PATENT DOCUMENTS

WO    WO 98/28430    7/1998

OTHER PUBLICATIONS

Byzova et al (2004, Planta 218:379-387).*
Yao et al (2001, PNAS 98(3): 1306-1311).*
Acciarri et al. "Genetically modified parthenocarpic eggplants: improved fruit productivity under both greenhouse and open field cultivation." *BMC Biotechnology*. vol. 2. 2002. pp. 1-7.
Ampomah-Dwamena et al. "Down-Regulation of TM29, a Tomato SEPALLATA Homolog, Causes Parthenocarpic Fruit Development and Floral Reversion." *Plant Physiology*. vol. 130. 2002. pp. 605-617.
Barg et al. "Differential regulation of a fruit-specific 62 kDA protein in developing parthenocarpic (pat-2/pat-2) and seeded tomato fruits." *Physiologia Plantarium*. vol. 80. 1990. pp. 417-424.
Bianchi et al. "Mutanti di Pomodoro Artificialmente Indotti suscettibili di Utilizzazione nel Miglioramento genetico." *Sementi Elette XV*. vol. 3. 1969. pp. 2-6.
Bowman et al. "Genes Directing Flower Development in *Arabidopsis*." *The Plant Cell*. vol. 1. 1989. pp. 37-52.
Clough et al. "Floral dip: a simplified method for Agrobacterium-mediated transformation of *Arabidopsis thaliana*." *The Plant Journal*. vol. 16. No. 6. 1998. pp. 735-743.
Coombe et al. "The Development of Fleshy Fruits." *Ann. Rev. Plant Physiol*. vol. 27. 1976. pp. 507-528.
Chandler et al. "Acid Citrus Fruit Cultivar Improvement Via Interploid Hybridization." *Proc. Fla. State Hort. Soc.* vol. 113. 2000. pp. 124-126.
Deng et al. Advances in breeding and selection of seedless types of Citrus in China. *Acta Hortic. Sin*. vol. 23. 1996. pp. 235-240. Abstract provided.
Deng et al. "Citrus Biotechnology Research in China." *Acta Horticulturae*. vol. 403. 1995. pp. 84-89.
Donzella et al. "Transgenic parthenocarpic eggplants: superior germplasm for increased winter production." *Molecular Breeding*. vol. 6. 2000. pp. 79-86.
Espinoza et al. "Gene expression associated with compatible viral diseases in grapevine cultivars." *Funct Integr. Genomics*. vol. 7. 2007. pp. 95-110.
Ficcadenti et al. "Genetic engineering of parthenocarpic fruit development in tomato." *Molecular Breeding*. vol. 5. 1999. pp. 463.470.
Franks et al. "Regeneration of transgenic *Vitis vinifera* L. Sultana plants: genotypic and phenotypic analysis." *Molecular Breeding*. vol. 4. 1998. pp. 321-333.
Gamborg et al. "Nutrient requirements of suspension cultures of soybean root cells." http:/www.sciencedirect.com/science?_ob=ArticleURL&udi=B6WFC-4F029RN-1. 2008.
Garcia-Martinez et al. "Gibberellins and fruit development." *Clarendon Press*. Oxford. 1997. pp. 263-285.
George, Jr. "Parthenocarpy in Tomato." *Hortic Rev*. vol. 6. 1984. pp. 65-84. Gillaspy et al. "Fruits: A Developmental Perspective." *The Plant Cell*. vol. 5. 1993. pp. 1439-1451.
Gibaeut et al. "Maximal Biomass of *Arabidopsis thaliana* Using a Simple, Low-Maintenance Hydroponic Method and Favorable Environmental Conditions." *Plant Physiol*. vol. 115. 1997. pp. 317-319.
Goes da Sliva et al. "Characterizing the Grape Transcriptome. Analysis of Expressed Sequence Tag from Multiple *Vitis* Species and Development of a Compendium of Gene Expression during Berry Development." *Plant Physiology*. vol. 139. 2005. pp. 574-597.

(Continued)

*Primary Examiner* — Stuart F. Baum
(74) *Attorney, Agent, or Firm* — Merchant & Gould P.C.

(57) ABSTRACT

Genes VvPI from *Vitis vinifera* cv. Cabernet Sauvignon and LePI from *Lycopersicon esculentum* are described; together with the use of these genes to produce sterile male flowers and seedless or parthenocarpic fruits. Silencing vectors that comprise these sequences or a part thereof are disclosed. The methods of the invention are directed to producing sterile male flowers and parthenocarpic fruits by genetic silencing, and includes: obtaining the codifying sequence of Pistillata (PI)-homologous genes from the target species; analyzing the expression of the sequence obtained in step (a) to test its expression according to the pattern described for Pistillata genes; analyzing the complementation of PI-gene mutant with the PI sequence obtained from the target species, to assess that the obtained sequence fulfills the function of a PI gene; making a genetic silencing construct that comprises a region of the codifying sequence of PI in a plant expression vector; incorporation of the constructed vector into *Agrobacterium tumefaciens*; transforming target plants with *Agrobacterium tumefaciens* modified with the silencing vector and selecting said transformed plants; and checking the absence of *Agrobacterium* contamination and corroborating transgenic plants by transgene amplification.

10 Claims, 1 Drawing Sheet

OTHER PUBLICATIONS

Guo et al. "Somatic hybrids between navel orange (*Citrus sinensis*) and grapefruit (*C. paradisi*) for seedless triploid breeding." *Euphytica* vol. 116. 2000. pp. 281-282.

Honma et al. "Complexes of MADS-box proteins are sufficient to convert leaves into floral organs." *Letters to Nature*. vol. 409. 2001. pp. 525-529.

Inoue. "On the flowering habit and anthesis behavior of *Kaga aonaga* cucumbers." *Agriculture and Horticulture*. vol. 18. No. 1. 1943. pp. 15-16.

Kaufmann et al. "MIKC-type MADS-domain proteins: structural modularity, protein interactions and network evolution in land plants." *Gene*. vol. 347. 2005. pp. 183-198.

Kihara et al. "Breeding of Seedless Fruits." *Seiken Ziho*. Japan. No. 9. 1958. pp. 1-7.

Kihara. "Triploid Watermelon." *Proceedings of the American Society for Horticultural Science*. vol. 58. 1951. pp. 217-231.

Koornneef et al. "Linkage map of *Arabidopsis thaliana*." *The Journal of Heredity*. vol. 74. 1983. pp. 265-272.

Liu et al. "Efficient Amplification of Insert End Sequences from Bacterial Artificial Chromosome Clones by Thermal Asymmetric Interlaced PCR." *Plant Molecular Biology Reporter*. vol. 16. 1998. pp. 175-181.

Lopez-Perez et al. "High embryogenic ability and plant regeneration of table grapevine cultivars (*Vitis*) *Vinifera* L.) induced by activated charcoal." *Vitis*. vol. 44. No. 2. 2005. pp. 79-85.

Lukyaneko. "Parthenocarpy in Tomato." *Genetic Improvement of Tomato*. Springer-Verlag—Germany. 1991. pp. 167-177.

Mazzucato et al. "The parthenocarpic fruit (pat) mutant of tomato (*Lycopersicon esculentum* Mil.) sets seedless fruits and has aberrant anther and ovule development." *Development*. vol. 125. 1998. pp. 107-114.

Mezzetti et al. "The defH9-iaaM auxin=synthesizing gene increases plant fecundity and fruit production in strawberry and raspberry." *BMC Biotechnology*. vol. 4. 2004. pp. 1-10.

Mezzetti et al. "Genetic Engineering of Parthenocarpic Fruit Development in Strawberry." *Proc. 4th Int. Strawberry Symp.* 2002. pp. 101-104.

Murashige et al. "A Revised Medium for Rapid Growth and Bio Assays with Tobacco Tissue Cultures." *Physiologica Plantarium*. vol. 15. 1962. pp. 473-497.

Nitsch et al. "Haploid Plants from Pollen Grains." *Science* vol. 163. 1969. pp. 85-87.

Nitsch. "Hormonal Factors in Growth and Development." *The Biochemistry of Fruits and their Products*. vol. 1. Academic Press—London and New York. 1970. pp. 427-472.

Nothmann et al. "Effects of growth regulators on fruit and see development in eggplant (*Solanum melongena* L.)" *J. Hort. Sci.* vol. 50. 1975. pp. 23-27.

Pandolfini et al. "Optimisation of transgene action at the post-transcriptional level: high quality parthenocarpic fruits in industrial tomatoes." *BMC Biotechnology*. vol. 2. 2002. pp. 1-11.

Pelaz et al. "B and C floral organ identity functions require SEPALLATA MADS—box genes." *Nature*. vol. 405. 2000. pp. 200-203.

Pelaz et al. "Conversion of leaves into petals in *Arabidopsis*." *Current Biology*. vol. 11. No. 3. 2001. pp. 182-184.

Philouze et al. "Natural parthenocarpy in tomato: Review of bibliography." *Agronomie*. vol. 3. No. 7. 1983. pp. 611-620.

Pnueli et al. "The TM5 MADS Box Gene Mediates Organ Differentiation in the Three Inner Whorls of Tomato Flowers." *The Plant Cell* vol. 6. 1994. pp. 175-186.

Porebski et al. "Modification of a CTAB DNA Extraction Protocol for Plants Containing High Polysaccharide and Polyphenol Components." *Plant Molecular Biology Reporter*. vol. 15. No. 1. 1997. pp. 8-15.

Romano et al. "The Responses of Tomato and Eggplant to Different Minimum Air Temperatures." *Acta Horticulturae*. vol. 366. 1994. pp. 57-63.

Rotino et al. "Genetic engineering of parthenocarpic plants." *Nature Biotechnology*. vol. 15. 1997. pp. 1396-1401.

Schaefer et al. "Enhanced resistance to early blight in transgenic tomato lines expressing heterologous plant defense genes." *Planta*. vol. 222. 2005. pp. 858-866.

Schwabe et al. "Hormones and parthenocarpic fruit set: A literature survey." *Horticultural abstracts*. vol. 51. No. 10. 1981. pp. 661-698.

Soressi et al. "A monomendelian gene inducing parthenocarpic fruits." *Rep.Tomato Genet. Coop.* vol. 25. 1975. pp. 22.

Sugiyama et al. "New Method of Producing Diploid Seedless Watermelon fruit." *JARQ*. vol. 36. No. 3. 2002. pp. 177-182.

Szechtman et al. "Seedless fruit setting in response to nam treatment of transgenic tomato expressing the iaaH gene specifically in the ovary." *Acta Hort.* vol. 447. 1997. pp. 597-598.

Vicient et al. "Isolation of Total RNA from *Arabidopsis thaliana* Seeds." *Analytical Biochemistry*. vol. 268. 1999. pp. 412-413.

Voinnet. "RNA silencing bridging the gaps in wheat extracts." *TRENDS in Plant Science*. vol. 8. No. 7. 2003. pp. 307-309.

Watanabe et al. "Effect of Cropping Season on the Formation of Empty Seeds in Seedless Watermelon Fruits Produced by Soft-X-Irradicated Pollen." *ACTA Hort*. vol. 588. 2002. pp. 89-92.

Yao et al. "Parthenocarpic apple fruit production conferred by transposon insertion mutations in a MADS-box transcription factor." *PNAS*. vol. 98. No. 3. 2001. pp. 1306-1311.

\* cited by examiner

Genomic VvPI
2134 bp

SEQUENCE LISTING

<160> NUMBER OF SEQ ID NOS: 7

<210> SEQ ID NO 1
<211> LENGTH: 2134
<212> TYPE: DNA
<213> ORGANISM: Vitis vinifera cv. Cabernet Sauvignon
<220> FEATURE:
<221> NAME/KEY: misc_feature
<222> LOCATION: (697)..(697)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (793)..(793)
<223> OTHER INFORMATION: n is a, c, g, or t
<220> FEATURE:
<221> NAME/KEY: misc_feature
<222> LOCATION: (1089)..(1089)
<223> OTHER INFORMATION: n is a, c, g, or t

<400> SEQUENCE: 1

```
atggggagag ggaagattga gatcaagagg atcgagaact caagcaacag gcaggtgacc      60
tactcaaaga ggagaaatgg gatcatgaag aaggccaagg agatcactgt tctctgcgat     120
gctcatgtct ctcttgttat ctttgctagc tctggaaaga tgcacgagta ctgtagccct     180
tctacaacgt atggagttct tttttttcct tcctggatat ttgtttcttt gatttaatcc     240
ttctgggttt tctttgtttt tctaactccc tcttttcctg ggttttttcc catgtgggtg     300
ctttcatctg gtgaaggttg attgatatct tggataggta tcacaagcag tctgggaaga     360
ggctctggga tgcaaaacat gaagtgggtt tgattctttg atatattttc cccactcttc     420
ctgtcatttt ttttatttgt aaaagcatct ggagtttctt gtttgtccca gtggaaaatg     480
acatacttct tttgctaaaa acatgttaag gaacacgaaa tatgaattct atgaacagat     540
ctcttcatga gcatgcctct tgtaaatgtc tgttaagatg tactaactgt taagggaaaa     600
actcagaaaa tctcagcaat gaattggata ggatcaaaaa ggagaatgat agcatgcaga     660
ttgaactcag gtagatagat ctctccttct ctttagnttc atctctctct ctctctttta     720
cttacatgta tgttacagga gatagatctc tccttctcnt agttcatctc tctctctctc     780
ttttattaca tgntgtaaag gcacctgaag ggggaggata tctcatctct gcaccacaaa     840
gaactcatgg ccattgagga tgcccttgag attggccttg caagtgttcg caacaaacag     900
gcaagttctc tcacactgta atattttaca tacacattgg ttgaagttct gaagagataa     960
tatcccaaat aacttctgat cttccccctt tgtgacaggc aagttctctc acactgtaat    1020
attttacata cacattggtt gaagttctga agagataata tcccaaataa cttctgatct    1080
tctcccttng tgacagatgg aattctacaa gatggtcaag aaaaattatt ttacatacac    1140
attggttgaa gttctgaaga gataatatcc caaataactt ctgatcttcc cccttgtga    1200 cagatggaat tctacaagat ggtcaagaaa aatgtatgta tagagtctat aaccagacaa    1260
acaattatcc catggaagat cttaaattct tgcctttgtt ttgatggggt tgtcattggc    1320
ttgttggcct atatttgtct ctatggttgc ttctttgatc tacaaatacc aaagagaggg    1380
agagagaaaa aaaatttcaa ttttgttcat gttcctaagt aggttaaaga tttgctagtt    1440
gcctaacttc tttattttg ggtgaacatt ctcagcaacg aatcctggag gaggagaaca    1500
agcacctcaa ttcatcgtg gtatgttatt atcacaatac attattaaca cacttaacac    1560
```

-continued

```
attcgtgtat atgggataaa aaaggtgtag atgtacatgg aaggaaatgt tcgtagtttc     1620
ttctttctat cgcatggttc atctatatat tctattcatg gtcatgtcac cggaaaatgt     1680
tctagctaga acaccgtcta ctagttttga acttcatatt aataattgtt catccaacaa     1740
agaagctggc cgggcaggac tccctgaatt gttttgttta ttgtctgcag caccaccagg     1800
gtatgcccat ggaggcgggc aatgtgagag aggtggaaag tggatatcat cagagagctg     1860
tgagggacta caatcccag atgcctttcg ccttccgggt gcagccaatt cagccaaact     1920
tacaggagag gatataactc tcttagctat atatatagtt tgtgctttaa ttaagaagga     1980
tacattccag acttgcaata gggtttgttg tagaggtgat cttattctcc ttcagccatt     2040
accctcaaaa cttataataa ttaaggtgtg tgatcttggt ttgtgaaact ttatatatat     2100
atatatatat atctttgaat gcttgctgac tacc                                2134
```

<210> SEQ ID NO 2
<211> LENGTH: 639
<212> TYPE: DNA
<213> ORGANISM: Vitis vinifera cv. Cabernet Sauvignon

<400> SEQUENCE: 2

```
atggggagag ggaagattga gatcaagagg atcgagaact caagcaacag gcaggtgacc       60
tactcaaaga ggagaaatgg gatcatgaag aaggccaagg agatcactgt tctctgcgat      120
gctcatgtct ctcttgttat cttgctagc tctggaaaga tgcacgagta ctgtagccct       180
tctacaacgt tgattgatat cttggatagg tatcacaagc agtctgggaa gaggctctgg      240
gatgcaaaac atgaaaatct cagcaatgaa ttggatagga tcaaaaagga gaatgatagc      300
atgcagattg aactcaggca cctgaagggg gaggatatct catctctgca ccacaaagaa      360
ctcatggcca ttgaggatgc ccttgagatt ggccttgcaa gtgttcgcaa caaacagatg      420
gaattctaca agatggtcaa gaaaaatcaa cgaatcctgg aggaggagaa caagcacctc      480
aattacatcg tgcaccacca gggtatgccc atggaggcgg gcaatgtgag agaggtggaa      540
agtggatatc atcagagagc tgtgagggac tacaatcccc agatgccttt cgccttccgg      600
gtgcagccaa ttcagccaaa cttacaggag aggatataa                             639
```

<210> SEQ ID NO 3
<211> LENGTH: 109
<212> TYPE: DNA
<213> ORGANISM: Vitis vinifera cv. Cabernet Sauvignon

<400> SEQUENCE: 3

```
ctctcttagc tatatatata gtttgtgctt taattaagaa ggatacattc cagacttgca       60
atagggtttg ttgtagaggt gatcttattc tccttcagcc attccctcc                  109
```

<210> SEQ ID NO 4
<211> LENGTH: 237
<212> TYPE: DNA
<213> ORGANISM: Vitis vinifera cv. Cabernet Sauvignon
<220> FEATURE:
<221> NAME/KEY: misc_feature
<222> LOCATION: (15)..(15)
<223> OTHER INFORMATION: n is a, c, g, or t

<400> SEQUENCE: 4

```
tagtgtagta gcagnagagc agataatggc agtttggctt ggctatgtca acaacccata       60
aacaagtcgt ccattctgtg gctctggaaa gttcattatc ccccaactta tattggaatg      120
ctcctccatt actttccttt cttttctctt ttcactgctt ttagtccttt atatcatctc      180
```

```
tccaggaaga ggaggaagaa gagaaagaga gaagaagagg gtttggtttg gagagag     237
```

```
<210> SEQ ID NO 5
<211> LENGTH: 212
<212> TYPE: PRT
<213> ORGANISM: Vitis vinifera cv. Cabernet Sauvignon

<400> SEQUENCE: 5
```

```
Met Gly Arg Gly Lys Ile Glu Ile Lys Arg Ile Glu Asn Ser Ser Asn
1               5                   10                  15

Arg Gln Val Thr Tyr Ser Lys Arg Arg Asn Gly Ile Met Lys Lys Ala
            20                  25                  30

Lys Glu Ile Thr Val Leu Cys Asp Ala His Val Ser Leu Val Ile Phe
        35                  40                  45

Ala Ser Ser Gly Lys Met His Glu Tyr Cys Ser Pro Ser Thr Thr Leu
    50                  55                  60

Ile Asp Ile Leu Asp Arg Tyr His Lys Gln Ser Gly Lys Arg Leu Trp
65                  70                  75                  80

Asp Ala Lys His Glu Asn Leu Ser Asn Glu Leu Asp Arg Ile Lys Lys
                85                  90                  95

Glu Asn Asp Ser Met Gln Ile Glu Leu Arg His Leu Lys Gly Glu Asp
            100                 105                 110

Ile Ser Ser Leu His His Lys Glu Leu Met Ala Ile Glu Asp Ala Leu
        115                 120                 125

Glu Ile Gly Leu Ala Ser Val Arg Asn Lys Gln Met Glu Phe Tyr Lys
    130                 135                 140

Met Val Lys Lys Asn Gln Arg Ile Leu Glu Glu Asn Lys His Leu
145                 150                 155                 160

Asn Tyr Ile Val His His Gln Gly Met Pro Met Glu Ala Gly Asn Val
                165                 170                 175

Arg Glu Val Glu Ser Gly Tyr His Gln Arg Ala Val Arg Asp Tyr Asn
            180                 185                 190

Pro Gln Met Pro Phe Ala Phe Arg Val Gln Pro Ile Gln Pro Asn Leu
        195                 200                 205

Gln Glu Arg Ile
    210
```

```
<210> SEQ ID NO 6
<211> LENGTH: 643
<212> TYPE: DNA
<213> ORGANISM: Lycopersicon esculentum

<400> SEQUENCE: 6
```

```
atggggagag ggaagattga gataaagaga atagaaaaca caaacaacag gcaagtaact      60
tattcaaaaa gaagaaatgg tataataaag aaagctaaag aaattactgt tctttgtgaa     120
gctaaggttt cacttataat ctttgctagt tctggaaaga tgcatgaata ttgtagccct     180
tctactacga taagtgatat gttggatggt tatcaaaaag cttctgggag gagactatgg     240
gatgctaagc atgagaattt gagtaatgaa attgataaga tcaagaaaga gaatgacagt     300
atgcaggtta agctcaggca cctcaaagga gaagatatca atcaacttac ccataaagag     360
cttataatta tggaagaagc cttacaaaat ggactttcta gtatcagtgc caagcagtct     420
gaaatcttga gatggtcagg aaaaatgatc aaattctgga ggaggaaaat aagcaacttc     480
aatatgcttt gcaccaaaag gagatgggag ccattggtgg aagtgaaaat atgagaggaa     540
ttcatgaaga aggtatcatc aaagagaaag ggattatgag taccaaatgc catttggcct     600
```

-continued

```
acgagtccag ccaatgcagc ctcatctaca tgaaagaatg taa                    643
```

<210> SEQ ID NO 7
<211> LENGTH: 214
<212> TYPE: PRT
<213> ORGANISM: Lycopersicon esculentum

<400> SEQUENCE: 7

```
Met Gly Arg Gly Lys Ile Glu Ile Lys Arg Ile Glu Asn Thr Asn Asn
1               5                   10                  15

Arg Gln Val Thr Tyr Ser Lys Arg Arg Asn Gly Ile Ile Lys Lys Ala
            20                  25                  30

Lys Glu Ile Thr Val Leu Cys Glu Ala Lys Val Ser Leu Ile Ile Phe
        35                  40                  45

Ala Ser Ser Gly Lys Met His Glu Tyr Cys Ser Pro Ser Thr Thr Ile
    50                  55                  60

Ser Asp Met Leu Asp Gly Tyr Gln Lys Ala Ser Gly Arg Arg Leu Trp
65                  70                  75                  80

Asp Ala Lys His Glu Asn Leu Ser Asn Glu Ile Asp Arg Ile Lys Lys
                85                  90                  95

Glu Asn Asp Ser Met Gln Val Lys Leu Arg His Leu Lys Gly Glu Asp
            100                 105                 110

Ile Asn Gln Leu Thr His Lys Glu Leu Ile Ile Met Glu Glu Ala Leu
        115                 120                 125

Gln Asn Gly Leu Ser Ser Ile Ser Ala Lys Gln Ser Glu Ile Leu Arg
    130                 135                 140

Met Val Arg Lys Asn Asp Gln Ile Leu Glu Glu Glu Asn Lys Gln Leu
145                 150                 155                 160

Gln Tyr Ala Leu His Gln Lys Glu Met Gly Ala Ile Gly Gly Ser Gly
                165                 170                 175

Asn Met Arg Gly Ile His Glu Glu Val Tyr His Gln Arg Glu Arg Asp
            180                 185                 190

Tyr Glu Tyr Gln Met Pro Phe Gly Leu Arg Val Gln Pro Met Gln Pro
        195                 200                 205

Asn Leu His Glu Arg Met
    210
```

METHOD TO PRODUCE STERILE MALE FLOWERS AND PARTENOCARPIC FRUITS BY GENETIC SILENCING, ASSOCIATED SEQUENCES AND VECTORS CONTAINING SAID SEQUENCES

BACKGROUND OF THE INVENTION

The present invention discloses a method to produce sterile male flowers and seedless or parthenocarpic fruits. This method is based on silencing genes that are homologous to Pistillata genes from different plant species, by generating silencing vectors that comprise the entire sequence of a Pistillata-homologous gene specific for the used species or a part of this sequence, and the use of said genetic silencing vectors to produce sterile male flowers and seedless or parthenocarpic fruits.

In the present invention, the sequences of VvPI gene from *Vitis vinifera* (grapevine) cv. Cabernet Sauvignon and LePI gene from *Lycopersicon esculentum* (tomato) are further disclosed, together with the use of these genes to produce sterile male flowers and seedless or parthenocarpic fruits. Furthermore, silencing vectors that comprise these sequences or a part thereof contained in said silencing vectors are disclosed, which allow silencing VvPI and LePI genes in *Vitis vinifera* cv. Cabernet Sauvignon and *Lycopersicon esculentum*, respectively.

VvPI from *Vitis vinifera* cv. Cabernet Sauvignon (grapevine) and LePI from *Lycopersicon esculentum* (tomato) are genes that are homologous to the Pistillata gene from *Arabidopsis thaliana*, which is a gene involved in petal and stamen formation in *Arabidopsis* and other flowers.

Seedless varieties have a high commercial value and improved organoleptic properties. Moreover, seedless varieties solve problems in some cultures, such as pollination. In the production of various cultivars, such as *Lycopersicon esculentum*, pollination use to be a critical step and even a limiting step for production, since this step is affected by wind, humidity and temperature, both in sub- or supra-optimal conditions (Nothman et al., 1975; Romano et al., 1994). Parthenocarpy offers an alternative route, because fruit development can occur independently from pollination (Lukyanenko et al., 1991) and thus it assures a greater stability to the producer.

In the majority of flowering plants, once pollination and subsequent fertilization have taken place, ovules develop to seeds, while the surrounding tissue differentiates to the fruit (Coombe et al., 1975). Fertilization is a critical step to begin flower-to-fruit transition, except for those parthenocarpic plants in which fruit development is uncoupled to fertilization. Parthenocarpic fruits develop without previous fertilization of the ovules, thus these ovules grow senescent and the ovary develops to a seedless fruit (Gillaspy et al., 1993).

Two are the phenomena associated with the apparition of seedless (apyrenic) fruits: parthenocarpy and stenospermocarpy. While parthenocarpy is the development and growth of a fruit without previous fertilization, stenospermocarpy is the apparition of seedless fruits or a reduced number of partially-formed seeds once fertilization has taken place, which is caused by an abortion of the seed during its formation.

The first methodology used to artificially create apyrenic fruits consisted of spraying developing fruits and even flowers, with auxins and gibberellins (GAs) (Nitsch et al., 1970; Schwabe et al., 1981; García-Martínez et al., 1997). However, the most used methodology to produce seedless fruits has been mutant selection. Many of these seedless mutant variants have been obtained by induced mutagenesis. For example, in tomato (*Lycopersicon esculentum*) different parthenocarpic lines have been produced in this way (reviewed by Lukyanenko et al., 1991). The most important cultivar line is the mutant obtained by using ethyl methane-sulfonate (Bianchi et al., 1969), called pat (parthenocarpic fruit) (Soressi and Salamini, 1975; Philouze et al., 1983; Barg et al., 1990; George et al., 1984; Lukyanenko et al., 1991).

Polyploidy has also been used, such as in triploid watermelon (Terada et al., 1943; Kihara et al., 1951, 1958) and citrus (Deng et al., 1996; Chandler et al., 2000; Guo et al. 2000) mutants. These mutants are generated by fusing protoplasts or crossing a tetraploid (4×) maternal plant with a diploid (2×) pollinator, thus generating a triploid (3×) individual that is then pollinated by a diploid plant to obtain seedless fruits. A more novel way comprises pollinating flowers with irradiated pollen. As was shown by Watanabe (2001) and Sugiyama (2002), this method allows obtaining diploid (2×) watermelon plants that produce fruits having few soft and small seeds, known as "empty seeds".

Lately, parthenocarpic fruits have been obtained using an approximation analogous to exogenous hormone application. The procedure comprises altering the phytohormone production pathway by introducing genes as iaaM, iaaH and rolB that increase internal hormone levels in the ovary, ovules and placenta. Szechtman et al. (1997) expressed gene iaaH from *Agrobacterium tumefaciens* specifically in tomato ovary. This gene codes for an indoleacetamide hydrolase that hydrolyzes naphthaleneacetamide (NAM) to naphthaleneacetic acid (NAA), an active auxin form. Thus, parthenocarpy was induced upon subsequently treating the ovary with NAM. Rotino et al. (1996) expressed a gene that codes for an enzyme involved in indol-3-acetic acid (IAA) biosynthesis that does not need any exogenous application of compounds. Said gene was the chimerical DefH9-iaaM gene, which has the codifying region of iaaM gene from *Pseudomonas syringae* pv. *savastanoi* and the placenta and ovule-specific promoter region DefH9 from *Antirrhinum majus* (Rotino et al., 1996). Gene iaaM codes for an enzyme, tryptophan monooxygenase, that produces indoleacetamide. Indoleacetamide is then enzymatically or chemically converted into the IAA auxin. Tobacco (Rotino et al., 1997), eggplant (Donzella et al., 2000; Rotino et al., 1997; Acciarri et al., 2002), *Lycopersicon esculentum* (Ficcadenti et al., 1999; Pandolfini et al., 2002) and strawberry and raspberry (Mezzetti et al., 2002; 2004) transgenics that have the transgene DefH9-iaaM are parthenocarpic in nature.

It has been previously shown that parthenocarpic apple (*Malus domestica*) varieties: Rae Ime, Spencer Seedless and Wellington Bloomless, had one transposon-insertion mutation in the orthologous Pistillata (PI) gene: MdPI (*Malus domestica* Pistillata). Furthermore, this PI gene requires the expression of Sepallata to carry out its function in *Arabidopsis* (Honma and Goto 2000; Pelaz et al. 2000, 2001). Therefore, lack of expression of genes that are homologous to tomato Sepallata (such as TM29, Ampomah-Dwamena et al. 2002; and TM5, Pnueli et al. 1994), leads to parthenocarpic fruit development.

Genetic Silencing.

Genetic silencing is a natural mechanism that allows gene expression inhibition at DNA level (transcriptional genetic silencing) or at messenger RNA level (post-transcriptional genetic silencing, PTGS). Currently, procedures have been developed to allow inhibiting gene expression by PTGS in various organisms, including plants. To this end, silencing plasmid vectors are used (e.g., Hellsgate) that generate sense and antisense RNA strands, thus forming double strand RNAs in the cytoplasm, which induce silencing of the target gene that has a similar sequence to that of the double RNA (Voinet, 2003).

In this invention, this technology was used to induce silencing of Pistillata genes from *Vitis vinifera* and *Lycopersicon esculentum* (grapevine and tomato, respectively), which are genes codifying for transcriptional factors responsible for petal and stamen formation in flowers.

Among the closest documents to this invention, the following could be mentioned:

Vliet G., 1998 (Patent Application WO 98/24301): this document claims a method to produce seedless tomatoes by crossing two homozygote tomato plants that are recessive for parthenocarpy (pk,pk) and functional sterility (fs,fs) characteristics; this is a technique totally different to that disclosed in the present invention.

In Ito et al., 2002 (US Patent Application US 2002/0152495), a polynucleotide is described that comprises a sequence codifying for cytochrome P450, and when this sequence is expressed in a plant, a parthenocarpic phenotype is produced and furthermore a larger fruit is obtained; this technique also differs from that of the present invention in the type of gene used and the mechanism by which it operates.

BRIEF DESCRIPTION OF SELECTED SEQUENCES

Figure 1:
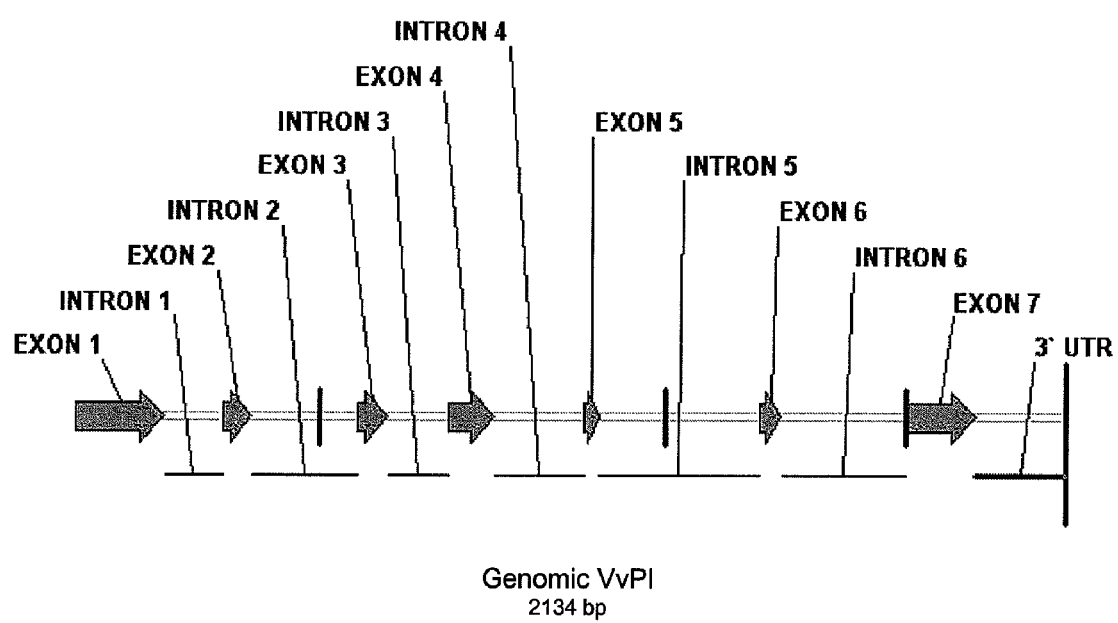
FIG. 1: Schematic representation of the exon-intron structure of the genomic cDNA sequence of VvPI gene from *Vitis vinifera*.

SEQ. ID. NO. 1: shows the genomic sequence of the Pistillata gene VvPI from *Vitis vinifera* cv. Cabernet Sauvignon.
SEQ. ID. NO. 2: shows the VvPI cDNA sequence from *Vitis vinifera* cv. Cabernet Sauvignon. SEQ. ID. NO. 3: shows the sequence of the 3'UTR region of gene VvPI from *Vitis vinifera* cv. Cabernet Sauvignon.
SEQ. ID. NO. 4: shows the sequence of the 5'UTR region of gene VvPI from *Vitis vinifera* cv. Cabernet Sauvignon.
SEQ. ID. NO. 5: shows the inferred amino acid sequence of VvPI protein from *Vitis vinifera* cv. Cabernet Sauvignon.
SEQ. ID. NO. 6: shows the cDNA sequence of LePI from *Lycopersicon esculentum*.
SEQ. ID. NO. 7: shows the amino acid sequence of LePI protein from *Lycopersicon esculentum*.

The Sequence IDs are further described starting on page 29.

SUMMARY OF THE INVENTION

The present invention discloses a method to produce sterile male flowers and parthenocarpic fruit, based on genetic silencing of a gene homologous to a Pistillata gene in a target species. Genetic silencing is produced by transformation of the target plant with a silencing vector that contains the entire sequence of a Pistillata homologous gene or a part thereof.

The present invention further discloses the sequences of VvPI gene from *Vitis vinifera* and LePI gene from *Lycopersicon esculentum*; these sequences can be seen as SEQ. ID NO. 1, 2, 3, 4 and 6. Genes VvPI and LePI are homologous to the MADS-box-type Pistillata gene (PI, *Arabidopsis thaliana*). Gene PI is involved in petal and stamen formation in *Arabidopsis* flowers. The present invention discloses the complete codifying region from both species. Besides having high amino acid identity when compared to PI, these genes also have the four typical domains of MADS genes: M, I, K and C; and the domain features of PI genes (Kaufmann et al., 2005). The present invention also discloses the use of these sequences to produce sterile male flowers, as well as silencing vectors containing these sequences, both as complete genetic sequences or as a part of the aforementioned sequences.

The present invention also discloses a method that allows developing sterile male flowers and parthenocarpic fruits, preferably to develop sterile male flowers and parthenocarpic fruits from e.g., but not limiting to, *Lycopersicon esculentum* and *Vitis vinifera*, by blocking the Pistillata gene function of the target species, which is involved in floral development, by genetic silencing.

The method to silence the expression of the target gene comprises amplifying nucleotide sequences of Pistillata-homologous genes from the target species, and subsequently expressing said sequences in vectors that induce silencing of the target genes. The phenotype of the target species is the production of sterile male flowers, i.e. flowers with no male organs, and therefore sterile plants and seedless fruits.

The methodology to produce sterile male flowers and seedless fruits can be synthesized in the following general steps:
a) obtaining the codifying sequence of the Pistillata (PI)-homologous gene from the target species;
b) analyzing the expression of the sequence obtained in step (a) to test its expression according to the pattern described for Pistillata genes;
c) analyzing the complementation of model PI-gene-mutant plants with the PI sequence obtained in the former stages from the target species, to assess that the obtained sequence fulfills the function of a PI gene;
d) making a genetic silencing construct that comprises a region of the codifying sequence of PI obtained in a plant expression vector;
e) incorporating the vector constructed and obtained in step (d) into *Agrobacterium tumefaciens*;
f) transforming plants of the target species with *Agrobacterium tumefaciens* modified with the silencing vector and selecting said transformed plants;
g) assessing the absence of *Agrobacterium* contamination and corroborating transgenic plants by transgene amplification;

The previous steps are described with more detail as follows:
a) Obtaining of the Codifying Sequence of the Pistillata (PI)-Homologous Gene from the Target Species Pistillata-homologous genes from the target species are cloned from cDNA obtained from inflorescences or immature flowers of the target species. cDNA is synthesized by reverse transcription from RNA. RT-PCR is carried out with the synthesized cDNA using degenerate primers, when the PI gene sequence of the target species is unknown; or specific primers, when the PI gene sequence of the target species is known, which can be constructed by methods well known to someone skilled in the art. For obtaining the entire gene sequence, RACE or TAIL PCR techniques are used. The obtained sequence is cloned into DNA cloning vectors and subsequently sequenced by any method known by someone skilled in the art. Each obtained sequence is tested by sequencing 4 to 6 different clones. Then, an in silico translation of the obtained sequence is made (by using computational tools) to generate the protein sequence, and this protein sequence is compared with other PI sequences described for other species, to obtain a sequence identity percentage, which is expected to be from 40 to 100%.

Given that PI genes belong to the MADS-box gene family, the translated sequence is then analyzed looking for the presence of domains that are typical of MIKC-type MADS-box proteins, i.e. MADS (M), Intervening (I), Keratin like (K) and C-terminal (C) domains. Furthermore, the motif known as PISTILLATA is looked for, which has an amino acid sequence FxFRLQPSQPNLH (SEQ ID. NO: 27), wherein x is any amino acid, and could be present or not in the PI homologous genes.

To assess that the translated sequence corresponds to a gene codifying for a PI protein, a phylogenetic analysis is performed on the sequence, comparing it with other sequences of previously described PI proteins and with other MADS-box non-Pistillata proteins. This analysis is performed with the help of computational programs, such as, e.g. PAUP software. The genomic sequence of the target genes can be obtained by amplification with degenerate or specific primers of DNA from the target species.

b) Analysis of the Expression of the Sequence Obtained in Step (a) to Test its Expression According to the Pattern Described for Pistillata Genes;

For the analysis of the obtained PI gene expression in the target plant, different tissues are collected, such as leaves, stems, roots, fruits, seeds or flowers, or different development stages of the inflorescence or the flower of the target plant are collected. Subsequently, techniques such as Northern blot or RT-PCR are used to evaluate gene expression. In the case of Northern blot, RNA is extracted from the tissues or developmental stages to be used. In the case of RT-PCR, extracted RNA is used to synthesize cDNA by reverse transcription. Northern hybridization membranes are hybridized with specific probes for known Pistillata genes with sizes from 200 to 800 bp, at a temperature from 40 to 70° C. RT-PCR amplifications use alignment temperatures from 48 to 65%, and also use specific primers to amplify a particular Pistillata gene, obtained from the Pistillata gene sequence from the target species found in the former stage. For both techniques, control genes should be used (e.g., actin) that allow assessing RNA and cDNA integrity.

c) Analysis of PI-Gene-Mutant Complementation with the Pistillata Sequence Obtained in the Former Stages from the Target Species, to Assess that the Obtained Sequence Fulfills the Function of a Pistillata Gene A function complementation assay with the obtained PI gene is performed in mutant plants for this gene, such as the *Arabidopsis thaliana* model species PI mutant, to assess that the obtained sequence fulfills the function of a typical PI gene. In this experiment, a mutant phenotype reversion is expected to occur; mutant model plants do not express the gene and therefore do not have petals and stamens in their flowers, and so, when the PI gene sequence from the target species obtained in stage (a) is incorporated under the control of a suitable promoter in mutant plants, the plants are expected to show morphological changes that could vary from little changes in cellular types of flower tissues to changes that imply development of petals and stamens.

To this end, a construct is made to contain the sequence codifying for the obtained PI gene of the target species (considering from the start ATG codon to the stop codon, or adding 5'UTR and 3'UTR regions to the codifying sequence) under a regulatory promoter sequence that could be a tissue-specific, inducible or strong constitutive expression sequence.

The obtained construct containing the PI gene from the target species under a regulatory promoter sequence is inserted in a vector that will further incorporate a selection marker into the plants such as, e.g., a determined antibiotic resistance. This vector is subsequently passed into an *Agrobacterium tumefaciens* bacterium by means of, for example, but not limiting to, electroporation, to allow plant transformation. Plants containing a PI gene mutation are used, such as, e.g., *Arabidopsis* PI mutant plants. Model plants heterozygous for a PI mutation are transformed and the seeds of these plants (F1) are analyzed. The seeds that are effectively transgenic should be resistant to the selection marker incorporated into the vector and therefore should germinate. In these plants, mutant phenotype complementation is looked for. In this F1 generation wild-type, heterozygous and PI mutant plants will be found. Therefore, plants must be genotyped to identify those that are homozygous for PI mutation and then the target transgene presence is assessed in these plants by means of PCR using specific primers for said transgene. The transformation technique to be used will depend on the model plant used. For example, when *Arabidopsis thaliana* is the model plant species, the "Floral dip" technique could be used.

Then, in plants that are PI mutant and transgenic for the target PI gene, the flower structure is analyzed to find a mutant phenotype reversion; this analysis is performed both with the naked eye and by using magnifying glasses and electron scanning microscopes. In the flowers of transformed plants, cellular types or organs are present which are not present in flower of mutant plants, such as, e.g., cell with petal cell or stamen cell morphology, or also the entire organs are present. It is also possible to transform directly vegetative tissue of mutant plants and wait for the development of a flower to analyze it as described before.

The steps to perform complementation are the following:
a) obtaining the Pistillata codifying sequence from the target species;
b) making a construct containing the PI gene from the target species in an expression vector that contains a promoter suitable for plants, such as pCAMBIA 1302;
c) incorporating the transformed vector into *Agrobacterium tumefaciens*;
d) transforming a model plant having a PI mutation (e.g., *Arabidopsis thaliana* ecotype Ler, heterozygous for pi-1 mutation). The transformation method will depend on the model plant used.
e) selecting transgenic seeds in Petri dishes with MS medium having the specific antibiotic of the resistance conferred by the vector or the appropriate selection marker, the plants being grown in growing chambers at a light intensity suitable for the chosen species;
f) identifying model plants homozygous for their PI gene mutation by PCR and/or enzymatic digestion;
g) assessing transgeny of plants identified in (f) by means of PCR over DNA, using specific primers to amplify a specific vector region that contains the transgene, under standard PCR conditions;
h) observing the floral phenotype of PI mutant plants complemented with the PI gene of the target species. Observation is made both at a macroscopic level in the flowers and using electron scanning microscopy for cell structures in all flower tissues.

d) Generating a Genetic Silencing Construct that Comprises a Region of the Codifying Sequence of Pistillata in a Plant Expression Vector With the aim of obtaining sterile male flowers and parthenocarpic fruits, a genetic silencing construct is designed that allows blocking the Pistillata gene function in transgenic target plants. This construct expresses a region or fragment of the PI homologous sequence found in the target species obtained in step (a), for example, the 3'UTR region, the codifying region or a part thereof or the 5'UTR region, both sense and antisense, with the aim of producing double stranded RNA and forming hairpins that lead to post-transcriptional genetic silencing. Specific sequences are added to the specific sequence fragment to be used that will be recognized in a silencing vector; these sequences or sites will allow including both the sense and antisense fragments to form the silencing hairpin. Apart from the silencing construct, the vector must contain genes that confer features to the plants that allow discriminating between transgenic and non-transgenic plants, such as, e.g., antibiotic resistance. The corroboration of the sequence that will form the silencing hairpin is performed by PCR and sequencing.

e) Incorporation of the Constructed Vector into *Agrobacterium tumefaciens*

The construct for genetic silencing that contains a region of the target PI gene sequence is incorporated into an expression vector for plants; this vector is transferred into a competent *Agrobacterium tumefaciens* strain for plant transformation. To this, the silencing gene comprising plasmid DNA that carries a region of the target species Pistillata gene is transferred into *Agrobacterium tumefaciens* by using a technique such as electroporation. If electroporation is used, 60 to 300 μl of the modified *Agrobacterium tumefaciens* strain are placed in an electroporation cell together with 0.5 to 3 μl of the purified silencing vector. The cell is placed in an electroporator and a voltage of 1.8 to 2.3 KV is applied for 5 to 7 ms. After this time, 600 μl to 1 ml of bacteria culture medium is added into the cell. Then the cell content is collected in a centrifuge tube which is placed in a shaker at 27 to 30° C. and 80 to 150 rpm for 3 hours. The previous culture must be centrifuged at a speed from 3,000 to 6,000 rpm for 2 to 12 minutes, and placed in a Petri dish containing bacterial growth medium supplemented with the selection antibiotics for the *Agrobacterium tumefaciens* strain that has been transformed with the silencing gene. Petri dishes are placed at 27 to 30° C. for 30 to 60 hours. The selection antibiotics must be specific for the *Agrobacterium tumefaciens* strain and silencing vector used, e.g. when using *Agrobacterium tumefaciens* strain GV3101 and silencing vectors pHELLSGATE 2, 8 or 12, the culture medium must be supplemented with the antibiotics: gentamicin, rifampicin and spectinomycin (according to manufacturer's instructions), wherein the first two antibiotics are related to selection of the *Agrobacterium tumefaciens* strain and the latter is related to vector selection. Bacterial colonies to be used are assayed by PCR with specific primers to test for the presence of the transgene.

f) Transformation of Plants of the Target Species with *Agrobacterium tumefaciens* Modified with the Silencing Vector and Selection of Transformed Plants i) Preparation of *Agrobacterium tumefaciens*

Silencing genes-carrying *Agrobacterium tumefaciens* strains are taken from Petri dishes and grown from 27 to 30° C. with agitation from 80 to 150 rpm for 24 hours in liquid bacterial growth medium with selection antibiotics according to the vector and *Agrobacterium tumefaciens* strain used. The following day, the culture is centrifuged at 3,000 to 6,000 rpm for 6 to 10 minutes, and cells are resuspended in plant specific liquid culture medium modified with acetosyringone 70 to 200 μM and placed at 25-30° C. with agitation from 80 to 150 rpm until reaching an optical density at 600 nm between 0.5-0.7.

This culture medium will depend on the target species, e.g. for *Lycopersicon esculentum* this liquid culture medium will comprise only sucrose, macro and micronutrients from MS culture medium (Murashige and Skoog 1962). For *Vitis vinifera* floral explants (anthers and ovaries from inflorescences), the liquid culture medium to be used is GS1CA (Franks et al. 1998), comprising macro and microelements from NN medium (Nitsch and Nitsch 1969), 60 g/L sucrose, pH 5.8 adjusted with NaOH and autoclaved.

ii) Preparation of the Explant to be Transformed

The explant to be transformed will depend on the target species, e.g. anthers, ovaries, cotyledons, hypocotyls, roots, embryos, embryogenic calli and the like. The explant preparation will also depend on the species and tissue to be used.

iii) Explant Transformation

The explant is immersed in the bacterial resuspension previously prepared which contains the transformed *Agrobacterium tumefaciens* strain and is placed at 25 to 30° C. in shakers with agitation of 90-100 rpm. The time elapsed during the infection process fluctuates between 15 minutes and 24 hours, depending on the species to be transformed. After *Agrobacterium tumefaciens* infection, the explants are dried with sterile absorbent paper and transferred to co-culture medium (regeneration medium for the transformed species with 50-100 μM of acetosyringone) during 1 to 14 days at 22-30° C. in the dark. The excess of *Agrobacterium tumefaciens* is removed by washing the transformed explants 4 times with sterile distilled water containing a specific antibiotic to eliminate *Agrobacterium tumefaciens* (e.g., 1 mg/L timentin). Then, explants are passed to a specific culture medium for the target species, to which the antibiotic for which the vector confers resistance in the plant (e.g., kanamycin, paramomycin, hygromycin and the like) must be added, and in this way it is possible to select the tissue that has effectively acquired the transgene. Furthermore, the medium must contain and antibiotic that allows removing *Agrobacterium tumefaciens* (e.g., timentin). These explants are kept in this medium for 20 to 90 days.

The explants are sub-cultured each 14 to 40 days and placed in a culture chamber with a photoperiod of 8-18 hours of light and 25-28° C. After some time, which is specific for the target species, e.g. 7 to 120 days, sprouts will appear from which those that are effectively transgenic will be able to grow, because they have incorporated the transgene that confers them resistance to the plant specific selection antibiotic. On the contrary, non-transgenic sprouts will not grow in the presence of the antibiotic; these sprouts must be sub-cultured in the specific medium for the target species together with the selection marker. When an antibiotic is not used as selection marker, it will be necessary to perform appropriate tests for the marker used in the vector.

g) Assessment of the Absence of *Agrobacterium tumefaciens* Contamination and Corroboration of Transgenic Plants by Transgene Amplification Transgenic sprouts grown according to which is described in the former step are used to assess the absence of *Agrobacterium tumefaciens* contamination; to this end, it is necessary to extract a little sample from the transformed plants, performing DNA extraction by means of any technique known by someone skilled in the art, and analyzing by using PCR for the presence of a bacteria-specific gene, such as the presence of vir genes. These bacteria-specific genes should not be amplified when bacterial contamination is not present.

Once confirmed the absence of bacterial contamination, it is necessary to analyze molecularly the presence of the transgene in the plants; to this end, a PCR amplification is carried out for a specific transgene region, which is the region of the target gene incorporated in the silencing vector; the primers used are the same than those used in the generation of the silencing vector that contain part of the recombination sites and part of the sequence of the PI gene used. In this step, amplification will be observed only in plants that have acquired the transgene.

Plants obtained from transgenic sprouts identified in step (f) and assessed in their transgeny in step (g) are conditioned and subsequently passed to greenhouse conditions on a substratum which will depend on the target species, such as, e.g., soil and perlite in a 1:1 ratio.

Example 1

Transformation of *Vitis vinifera* and *Lycopersicon Esculentum* to Obtain Sterile Male Flowers and Parthenocarpic Fruits a.—Obtaining of the Pistillata Codifying Sequence (PI) from *Vitis vinifera* cv. Cabernet Sauvignon and *Lycopersicon esculentum*

To obtain PI homologous genes from grapevine (*Vitis vinifera* cv. Cabernet Sauvignon) and tomato (*Lycopersicon esculentum*), known sequences of MADS-box genes were used to search for conserved domains and generating degenerate primers based on them, because these genes belong to the MADS-box family. Then two Pistillata-type genes were cloned and named VvPI and LePI for species *Vitis vinifera* cv. Cabernet Sauvignon and *Lycopersicon esculentum*, respectively, which apart of having a high amino acid identity to PI also possess the four typical domains of MADS-box genes: M, I, K and C; and the domain characteristic of PI genes.

The codifying regions (cDNA) of PI genes from both species were obtained from RNA from immature inflorescences for VvPI and pre-anthesis stage flowers for LePI. Both genes, VvPI and LePI, were isolated by RT-PCR using degenerate primers, their sequences having been cloned in cloning vectors (pGEM-T Easy, Promega) and then sequenced. Each sequence was corroborated by sequencing at least four independent clones. Degenerate primers used to obtain the cDNA sequence of VvPI and LePI were generated by using the Vector NTI software ClustalW (version 8.0). Using matrix BLOSUM62, Pistillata from *A. thaliana* (AAD1995) and four Pistillata orthologous genes belonging to the species: *Malus domestica, Nicotiana tabacum, Antirrhinum majus* and *Betula pendula* (CAC28022, X67959, CAA48725, AJ488589, respectively) were aligned. In this analysis, a high identity cluster with high nucleotide identity was identified at the MADS-box 5' end, and another was identified at the 3' end, both having very conserved motifs among PI genes in the C-terminal end. These two clusters were used to design degenerate primers to identify the target genes; the synthesized primers were the following:

```
P1-5':
5'-ATGGGDMGWGGRAARRTHGA-3';    (SEQ ID. NO. 8)
and

P2-3':
5'-TTWGGCTGMATHGGYTGVAC-3';    (SEQ ID NO. 9)
wherein

W = GCT, R = AG, H = ACT, M = AC, V = ACG,
D = ATG, Y = CT.
```

While 3' regions from both genes were obtained by 3'RACE, 5' regions were obtained by using the TAIL-PCR technique with reaction conditions from Liu and Huang (1998). The genomic sequence of both genes LePI and VvPI was also obtained by PCR from genomic DNA of *Vitis vinifera* cv. Cabernet Sauvignon and *Lycopersicon esculentum*. DNA was obtained from young leaves using the CTAB extraction method (Porebski et al., 1997).

Both genes comprise 7 exons and 6 introns, and the relative positions are detailed in Table 1 and FIG. 1 for the VvPI gene (*Vitis vinifera* cv. Cabernet Sauvignon Pistillata).

TABLE 1

Exons and Introns of the VvPI gene

| | Exon | | Intron |
|---|---|---|---|
| 1st | 1 nt-189 nt | 1st | 190-317 |
| 2nd | 318-380 | 2nd | 381-605 |
| 3rd | 606-671 | 3rd | 672-801 |
| 4th | 802-900 | 4th | 901-1,096 |
| 5th | 1,097-1,126 | 5th | 1,127-1,520 |
| 6th | 1,476-1,520 | 6th | 1,421-1,790 |
| 7th | 1,791-1,937 | | |
| 3UTR | | 1,938-2,134 | |

By performing a computer-aided phylogenetic analysis of the sequence, using the PAUP software (Phylogenetic Analysis Using Parsimony) 4.0, it was determined that the sequence of *Vitis vinifera* cv. Cabernet Sauvignon should belong to family Pistillata/Globosa, which comprises all the described PI homologues.

From the former results and using the Vector NTI 4.0 software, the VvPI amino acid sequence was deducted, comprising 212 amino acids (SEQ ID No. 5). By aligning VvPI with other amino acid sequences obtained from PI homologous genes (carried out with the Vector NTI advance 10 software with the alignX application), it was shown that VvPI has all the typical domains of a MADS-box gene (MADS, Intervening, Keratin-like and C-terminal domains), and also has the Pistillata domain present in the major part of the described PI homologues. The same analysis found the aforementioned domains in the LePI sequence.

As an example, the identity percentage between the known Pistillata protein sequence from *Arabidopsis* with VvPI and LePI proteins is 49 and 53.3%, respectively.

Details of the cDNA sequence and the deducted protein sequence (obtained by using computational tools) of LePI are shown in SEQ ID No. 6 and 7.

b) Analysis of VvPI Gene Expression to Test its Expression According to the Pattern Described for Pistillata Genes VvPI gene expression found in step (a) and described in SEQ ID No. 2 was analyzed by RT-PCR using VvPI specific primers:

```
PID3    ATGGGGAGAGGGAAGATTGAG;    (SEQ ID NO: 10)
and

PID4    GTTTGGCTGAATTGGCTGCAC,    (SEQ ID NO: 11)
```

These primers were designed from the sequence obtained with the degenerate aforementioned primers.

These primers were used to perform RT-PCR in cDNA from different tissues from species *V. vinifera* cv. Cabernet Sauvignon. Analyzed tissues were leaves, roots, fruits, seeds and flowers. To perform the expression analysis, RNA was obtained by using the 8 M LiCl technique (Vicient and Delseny, 1999), and from this RNA cDNA was synthesized using random hexamers (Invitrogen) and the "StrataScript" reverse transcriptase enzyme following the manufacturer's instructions (Stratagene). To corroborate cDNA integrity, the constitutive G3PDH gene was amplified.

VvPI gene expression was only observed in floral tissue, in correspondence with that expected from the literature. VvPI gene expression exclusively in floral tissue was assessed by Northern blot (Goes da Silva et al., 2005); in this assay a 228-bp probe was used, which was synthesized using primers:

```
                                            (SEQ ID NO: 12)
VvPI 3'UTR (F):        GCAATGTGAGAGAGGTGGA;
and (SEQ ID NO: 13)
VvPI 3'UTR (R):        GAGGGTAATGGCTGAAGGAG.
```

These primers were designed from the sequence found in step (a) and described in SEQ ID No. 3.

As a constitutive gene control, the expression of G3PDH gene was analyzed to test that the RNAs used had a quality suitable to be used in the expression assay. In this assay, the VvPI expression exclusively in floral tissues was again assessed.

c) Analysis of PI-Gene-Mutant Complementation with the *Vitis vinifera* cv. Cabernet Sauvignon Pistillata Sequence Previously Obtained, to Assess that the Obtained Sequence Fulfills the Function of a Pistillata Gene To corroborate that VvPI is not only homologue to Pistillata but also orthologue to it (share the same function), a complementation assay was carried out in *Arabidopsis thaliana* PI-mutant plants (pi-1), looking for a reversion of the mutant phenotype.

Using the cloned VvPI gene sequence described in SE ID No. 2, from its ATG start codon to its TAA stop codon, a construct was made in the expression vector pCAMBIA 1302 (CSIRO, Australia), where a codifying sequence was put under the control of the constitutive 35S promoter (CAMV 35S) present in the vector.

The construct, called P35S-VvPI was constructed by amplifying VvPI from inflorescence cDNA using the primers:

```
P1ln:
AAGCTTAGATCTATGGGGAGAGGGAAGA;       (SEQ ID NO: 14)
and

P1fin2:
CACGTGTTATATCCTCTCCTGTAAGTT.        (SEQ ID NO: 15)
``` which introduce BglII and PmII sites in the 5' and 3' ends, respectively. The fragment was cloned in the vector pCAMBIA 1302 linearized with BglII and PmII, replacing the gfp gene by the VvPI gene. The vector confers resistance to the antibiotic hygromycin in plants that incorporate it.

*Agrobacterium tumefaciens* strain GV3101 with resistance to the antibiotic rifampicin was used. The vector previously developed was transferred to *Agrobacterium tumefaciens* strain GV3101 by electroporation. To this end, 80 µl of the *Agrobacterium tumefaciens* GV 3101 strain and 1 µl of a vector miniprep (obtained by using the vector extraction kit from "Marligen Bioscience" according to manufacturer's instructions) were placed in an electroporation cell (0.2 cm electrode). The cell was put in an electroporator with a voltage of 2.18 KV for 6.1 ms. After this time has elapsed, 1 ml LB medium (10 g/L Tryptone, 5 g/L yeast extract, 10 g/L NaCl) was added to the cell, the content of which was collected and placed in a centrifuge tube at 28° C. in shakers at 150 rpm for 3 hours. The construct P35S-VvPI was introduced in *Arabidopsis thaliana* ecotype Ler pi-1 mutation heterozygous plants (Koornneef et al., 1983); homozygous mutants for this mutation show an anomalous development of floral organs (verticils) except sepal development. The second verticil organs (petals) develop in little sepals instead of petals, the third verticil organs (stamens) do not develop and the central gynaeceum develops abnormally (Bowman et al., 1989). These plants do not express the PI gene, since they present an early stop codon. We have observed as expected that these plants develop a little seedless fruit in the absence of fertilization. The VvPI gene cDNA (639 bp) under the control of the constitutive promoter 35S (35SCaMV) in vector pCAMBIA 1302, present in *Agrobacterium tumefaciens* strain GV3101, was introduced in *Arabidopsis thaliana* pi-1 plants by the "Floral dip" technique (Clough S J, Bent A F. 1998). Flowers of heterozygous pi-1 *Arabidopsis thaliana* ecotype Ler mutants were immersed in a sucrose solution containing *Agrobacterium tumefaciens* transformed with the vector containing the VvPI transgene and having resistance to the antibiotic hygromycin. In this technique, germinal cells present in the flower are transformed, therefore transgenic plants are looked for in the first generation of plants obtained from the seeds generated by the transformed flowers.

The used transformation protocol, "Floral dip", has a duration of 4 days, wherein in the first day an inoculum of *Agrobacterium tumefaciens* strain GV3101 transformed with the vector containing the PI gene from *Vitis vinifera* cv. Cabernet Sauvignon (SEQ ID No. 2) (20 µl) was grown in 5 ml of bacterial YEP culture medium (10 g/L Bactopeptone, 10 g/L yeast extract, 5 g/L NaCl, pH 7) for 48 hours at 28° C. with shaking. The third day, 1 µl of the former 5 ml was taken and 200 ml of nutritive medium (YEP) with suitable bacterial and vector resistance antibiotics (rifampicin 10 mg/L and gentamicin 25 mg/L, respectively) were added. This solution was kept for 24 hours at 28° C. with shaking. On the fourth day, bacteria were decanted by centrifugation at 3,000 g for 10 min, and then resuspended in water with 5% sucrose and 0.05% surfactant.

Plant flowers were immersed in this solution for 10 seconds and then were placed in normal growing conditions (hydroponic medium according to Gibeaut et al., 1997, in culture chamber under 150 µmol m$^{-2}$ s$^{-1}$ of photosynthetically active radiation with 16/8 light-darkness hours at 24° C.). Seeds generated by these plants were grown in MS medium with 25 mg/L hygromycin to select transgeny, and then were passed into the hydroponic medium herein described. In these plants genotype was analyzed to search for homozygous pi-1 mutant plants by PCR amplification and enzymatic digestion. Then, the presence of transgene VvPI was assessed in plants by PCR. These plants showed a pi-1 mutation phenotype reversion, i.e. apparition of petal and stamen cells.

Furthermore, data present in the literature indicating pi-1 mutant plants showing formation of seedless fruits in absence of fertilization were corroborated, with a smaller size in comparison with fertilized fruits in wild-type plants. Fruits from mutant plants were analyzed by optical microscopy, testing the absence of seeds.

The process to perform complementation was the following:

a) Obtaining of the Pistillata codifying sequence (PI) from *Vitis vinifera* cv. Cabernet Sauvignon;

b) Introducing the construct P35S-VvPI in the pCAMBIA 1302 expression vector c) Incorporation of the transformed pCAMBIA 1302 vector into *Agrobacterium tumefaciens* strain GV3101;

d) Transformation by using the "Floral dip" technique of *Arabidopsis thaliana* pi-1 heterozygous mutant plants with the transformed *Agrobacterium tumefaciens* strain GV3101;

e) Selection of transgenic seeds in Petri dishes with MS medium having hygromycin (25 mg/ml), pH 5.7. Plants were grown in growth chambers at a luminous intensity of 40 µmol s$^{-1}$ m$^{-2}$;

f) Identification of pi-1 homozygous mutant plants (which have the transgene according to step (e)), by amplifying a 237-bp fragment by PCR in genomic DNA with primers (F)GPI-1 5'TACCAGAAGTTATCTGGCAA-GAAATCATG (SEQ ID NO: 16) and (R)PIntron-I1 5'CCAATTTCATGATATCTAGCTCAG (SEQ ID NO. 17), specific for the *Arabidopsis thaliana* PI gene, with PCR conditions: 94° C. for 3 minutes and then 35 cycles of 94° C. for 30 seconds, 55° C. for 40 seconds and 72° C. for 1 minute, followed by 10 final minutes at 72° C. The amplified fragment is cut by restriction enzymes EcoRV and BspHI, in a digestion reaction at 37° for 4 hours, wherein mutants present a 212-bp band in 4% agarose gels when BspHI is used;

g) Transgeny corroboration by PCR on DNA from the putative transgenic plants using specific primers for a region of the 35S promoter (ATGGTGGAGCACGA-CACTCTC) (SEQ ID NO: 18) and another primer for a specific region of gene VvPI (CCCAGAGCCTCTTC-CCAGACTGC) (SEQ ID NO: 19), with PCR conditions of 94° C. for 3 minutes and 35 cycles of 94° C. for 40 seconds, 56° C. for 1 minute and 72° C. for 1 minute and 30 seconds, with 7 minutes for final extension at 72° C.;

h) Observation of the floral phenotype of pi-1 mutant plants complemented with the VvPI transgene. This observation is carried out both at a macroscopic level in the flowers and using scanning microscopy for cell structures in all flower tissues.

The same process was applied to corroborate that LePI has the function of a PI gene.

Making the Genetic Silencing Construct Containing VvPI and LePI

To induce genetic silencing of VvPI and LePI genes in species *Vitis vinifera* cv. Cabernet Sauvignon and *Lycopersicon esculentum*, constructs IS::VvPI (Induced Silencing *Vitis vinifera* Pistillata gene) and IS::LePI (Induced Silencing *Lycopersicon esculentum Pistillata* gene), respectively.

For the construct IS::VvPI, a 250-bp fragment was amplified from cDNA, from nucleotides 390 to 639, which corresponds to the 3' region of the codifying region of VIP gene (SEQ ID No. 2). Regions attB1 and attB2 recognized by the clonase enzyme were added, which by recombination generate the fragment in the specific silencing vector pHELLGATE (CSIRO, Australia), both sense and antisense to form the silencing hairpin. This vector further confers resistance to the antibiotic paramomycin in transgenic plants.

For the construct IS::LePI, a 315-bp fragment was amplified from nucleotides 495 to 809 from cDNA SEQ ID No. 6, which comprises a 3'UTR region of the *Lycopersicon esculentum Pistillata* gene. Regions attB1 and attB2 recognized by the clonase enzyme were added, which by recombination introduce the fragment both sense and antisense in the vector Hellsgate 2 (CSIRO, Australia), thus generating a silencing hairpin. The corroboration of the sequence that form the silencing hairpin was performed by PCR and sequencing.

The generated vectors codify for resistance to the antibiotic spectinomycin in bacteria.

e) Incorporation of the Constructed Vectors into *Agrobacterium tumefaciens*

The silencing vector developed in step (d) is transferred into *Agrobacterium tumefaciens* GV3101 by electroporation. To this end, 80 µl of the *Agrobacterium tumefaciens* GV3101 strain and 1 µl of a silencing vector miniprep (obtained by using the vector extraction kit from "Marligen Bioscience" according to manufacturer's instructions) must be placed in an electroporation cell (0.2 cm electrode). The cell is put in an electroporator with a voltage of 2.18 KV for 6.1 ms. After this time has elapsed, 1 ml LB medium (10 g/L Tryptone, 5 g/L yeast extract, 10 g/L NaCl) must be added to the cell, the content of which was collected and placed in a centrifuge tube at 28° C. in shakers at 150 rpm for 3 hours.

The previous culture was centrifuged at 6,000 rpm for 3 minutes, and subsequently placed in a Petri dish containing LB medium enriched with antibiotics to select the *Agrobacterium* strain transformed with the silencing vector, i.e. 50 mg/L gentamicin and 10 mg/L rifampicin for *Agrobacterium* strain GV3101 and 50 mg/L spectinomycin for selection of vector IS::VvPI. The Petri dishes were placed at 28° C. for 48 hours.

The generated colonies were selected and tested by PCR using primers that amplify the VvPI gene region incorporated between attB sites, using the following specific primers:

```
                                            (SEQ ID NO: 20)
attB1-2   ACAAAAAAGCAGGCTCCTGGCCTTGCAAGTGTTCGC;
and (SEQ ID NO: 20)
attB2-1   ACAAGAAAGCTGGGTGGCTGAATTGGCTGCACCC.
```

These primers were designed to test the transformation success and comprise a specific region of the target sequence and part of the attB site required for recognition by the clonase enzyme, which by recombination generates the fragment in vector pHELLGATE 2. In the case of IS::LePI, fragments comprising the same attB site regions plus a specific region for the LePI fragment were used:

```
LePlatt B2
                                            (SEQ ID NO: 21)
ACAAGAAAGCTGGGTGGGAAGAGCCCATAAAATTAGG
and LePlatt B1
                                            (SEQ ID NO: 22)
ACAAAAAAGCAGGCTCCAAAAGGAGATGGGAGCC.
```

Therefore, these primers allowed determining the presence of the respective transgenes in transformed *Agrobacterium tumefaciens* strain GV3101.

f) Transformation of Plants of the Target Species with *Agrobacterium tumefaciens* Modified with the Silencing Vector and Selection of Transformed Plants i) Preparation of *Agrobacterium tumefaciens*

The *Agrobacterium tumefaciens* strain GV3101 were collected from Petri dishes and grown overnight at 28° C. and 150 rpm for 24 hours in LB medium enriched with selecting antibiotics: 50 mg/L gentamicin and 10 mg/ml rifampicin for *Agrobacterium tumefaciens* strain GV3101 and 50 mg/L spectinomycin for vectors IS::VvPI or IS::LePI. The next day the bacterial culture was centrifuged at 3,000 rpm for 10 minutes, resuspended in a plant culture medium; for *Lycopersicon esculentum* this culture medium only contained sucrose, macro and micronutrients from the MS culture medium (Murashige and Skoog 1962). For *Vitis vinifera* cv. Cabernet Sauvignon floral explants (anthers and ovaries from inflorescences), the liquid culture medium employed was GS1CA (Franks et al. 1998), containing macro and microelements from the NN medium (Nitsch and Nitsch 1969), 60 g/L sucrose, pH 5.8 adjusted with NaOH and autoclaved.

Grapevine Transformation:

ii) Preparation of the Tissue to be Transformed

Immature inflorescences from *Vitis vinifera* L. cv. Chardonnay from the experimental collection in field conditions of the Pontifical Catholic University of Chile were collected. Said samples were taken into the laboratory, placed at 4° C. for 48 h and subjected to an in vitro sterilization process (20% v/v sodium hypochlorite, agitation for 20 minutes, 4 rinses with sterile deionized water). Then, dissection of each flower was performed in sterile conditions, with the purpose of isolating anthers and ovaries, and subsequently culture them in vitro.

Embryogenic calli able to generate somatic embryos potentially viable to form a complete plant were obtained from the in vitro culture of anthers and ovaries, according to the methodology described by Franks et al. (1998). Initially, 100 anthers and 40 ovaries were placed in an embryogenic calli induction medium called PIV, containing: macro and microelements from the NN medium (Nitsch and Nitsch 1969), MS vitamins (Murashige and Skoog 1962), 60 g/L sucrose, the pH was adjusted to 5.8 with NaOH and 3 g/L gelrite (Sigma-Aldrich Co.) were added, the medium was autoclaved and 4.5 μM 2.4 D (2,4-dichlorophenoxyacetic acid) and 8.9 μM BA (benzylamino-purine) were added. Cultures were kept at 25° C. in the dark for three months and sub-cultured in fresh medium every 30 days. Then, the generated embryogenic calli were cultured in a differentiation and proliferation medium called GS1CA (solid culture medium). This medium contains: macro and microelements from the NN medium, MS vitamins, 60 g/L sucrose, 10 μM NOA, 1 μM BA, 20 μM IAA, 2.5 g/L activated charcoal (Merck), the pH was adjusted to 5.8 with NaOH and 5 g/L gelrite (Sigma-Aldrich Co.) were added. Cultures were kept at 25° C. in the dark for two months and subsequently sub-cultured in fresh medium every 30 days. Embryogenic calli were conserved for one year without losing their embryogenic ability, alternating every two months the PIV and GS1 CA culture media previously defined.

iii) Transformation of *Vitis vinifera* L. Embryogenic Calli with the Modified *Agrobacterium tumefaciens* Strain GV3101.

Embryogenic calli (100 g) with somatic embryos in globular state originated from the two months culture in solid medium GS1CA were immersed in the aforementioned bacterial resuspension (f-i) for 15 minutes at 28° C., 90 rpm. After infection with the modified *Agrobacterium* strain GV3101, the somatic embryos culture was dried with sterile absorbent paper 3MM. Subsequently, these embryos were transferred to a co-culture medium (GS1CA with 100 μM acetosyringone) during 48 hours at 28° C. in the dark. The *Agrobacterium tumefaciens* GV3101 excess was removed by rinsing 4 times the embryogenic calli with sterile modified proliferation culture medium GS1CA (described in ii) containing 1 mg/ml of the antibiotic timentin, which acts by inhibiting the growth of *Agrobacterium tumefaciens*. Embryogenic calli were collected from the liquid culture medium by using 100 μfilters (3M Nylon Net Filter) and cultured in solid culture medium GS1CA with 1 mg/ml timentin in the dark at 25° C. After 30 days, the embryogenic calli were sub-cultured in the same culture medium with 25 mg/L paramomycin for 30 days, allowing proliferation of calli over selection medium. After 60 days from inoculation, embryogenic calli were sub-cultured over the hormone-free GS1CA medium with 1 mg/L timentin and 25 mg/L paramomycin, which allows differentiating between plants that have acquired vector-conferred resistance and those that have not. Calli were kept for 30 days growing in the dark at 25° C. After this time, somatic torpedo stage embryos and mature embryos were cultured for 30 additional days in embryo germination medium, which contained microelements and half the concentration of macroelements from the MS medium, MS vitamins, 30 g/L sucrose, 2.5 g/L activated charcoal (Merck), the pH was adjusted to 5.8 with NaOH and 5 g/L gelrite (Sigma-Aldrich Co.) were added, the medium was then autoclaved and 10 μM IAA, 1 μM $GA_3$ (López-Pérez et al. 2005) were added. Cultures were kept at 25° C. with a photoperiod of 16 hours and photon density flux of 40 $\mu mol\ s^{-1}\ m^{-2}$.

Germinated embryos, which are those that have a bipolar structure with a radical-apical axe, hypocotyl elongation and green cotyledons, were cultivated for converting them into plants in Murashige and Skoog medium at half its salt concentration with 20 g/L sucrose, the pH was adjusted to 5.8 with NaOH, en 7.0 g/L agar (Merck) were added; cultures were kept at 25° C., with a photoperiod of 16 h and a photon flux density of 40 $\mu mol\ s^{-1}\ m^{-2}$. Subcultures were made every 30 days.

Transformation of *Lycopersicon esculentum* iv) Transformation of *Lycopersicon esculentum* Plants

Transformation of *Lycopersicon esculentum* was carried out following the procedure described by Shaefer et al., 2005. To this end, *Lycopersicon esculentum* seeds were disinfected with commercial 50% hypochlorite and put to germinate in vitro. After a week of culture, cotyledons were removed from recently germinated seedlings. These cotyledons were inoculated with *Agrobacterium tumefaciens* strain GV3101, which contained vector IS::LePI. Both the vector generation as the incorporation of this vector into *Agrobacterium tumefaciens* strain GV3101 were the same as those previously described for *Vitis vinifera* cv. Cabernet Sauvignon.

*Lycopersicon esculentum* explants together with bacteria were co-cultured for 2 days in MS medium containing 1 mg/L BAP, 0.1 mg/L IAA, 30 g/L sucrose, 20 mg/L acetosyringone, at pH 5.8, and 10 g/L agar (Merck) and placed in a culture chamber at 25° C., with a photoperiod of 16 h and photon flux density of 40 $\mu mol\ s^{-1}\ m^{-2}$. To stop the growth of *Agrobacterium tumefaciens* strain GV3101 and promote sprout formation, cotyledons were sub-cultured in the same MS medium but without acetosyringone and with the addition of 25 mg/L paramomycin and 1 mg/ml timentin, for 8 to 10 weeks. The obtained sprouts were sub-cultured periodically every 15 days in MS medium containing 25 mg/L paramomycin as selective agent and 1 mg/L timentin.

g.) g) Assessment of the Absence of *Agrobacterium* Contamination and Corroboration of Transgenic Plants by Transgene Amplification Before performing the detection assays for the transgene sequence in transformed plants, the presence of *Agrobacterium tumefaciens* strain GV3101 contamination was initially tested. To this end, embryogenic tissue (for *Vitis vinifera* cv. Cabernet Sauvignon) and leaves (for *Lycopersicon esculentum*) were selected. DNA was extracted from these tissues and a possible contamination with *Agrobacterium tumefaciens* strain GV3101 was tested by amplification of the sequence of VirG gene, which is present only in bacteria and not in plants. Accordingly, the absence of *Agrobacterium tumefaciens* GV3101 contamination was demonstrated.

To detect the presence of the transgenic silencing sequence for VvPI in plant tissue, said sequence was amplified using specific primers.

attB1-2 ACAAAAAAGCAGGCTCCTGGCCTTG-CAAGTGTTCGC (SEQ ID NO: 23); and attB2-1 ACAAGAAAGCTGGGTGGCTGAATTGGCT-GCACCC (SEQ ID NO. 24)

which allowed differentiating said sequence from the endogenous sequence. Genomic DNA used for PCR amplification reactions was isolated according to the procedure described in Espinoza et al., 2006.

For the case of *Lycopersicon esculentum*, the same procedure described for *Vitis vinifera* cv. Cabernet Sauvignon was carried out, but in this case using specific primers
LePlatt B2 ACAAGAAAGCTGGGTGGGAAGAGCCCATAAAATTAGG (SEQ ID NO: 25) and
LePlatt B1 ACAAAAAAGCAGGCTCCAAAAGGAGATGGGAGCC (SEQ NO: 26),
which allow amplifying the sequence of transgene LePI.

With this, the presence of the gene in transformed plants is checked.

Finally, plants obtained from transgenic sprouts, in the case of tomato, or from transgenic embryos, in the case of grapevines, according to that described in step (f), and in which transgeny was checked according to step (g), were rooted and transferred into a mixture of soil and perlite 1:1, where said plants were grown in a growth chamber at 25° C. These seedlings were protected from dehydration by covering them with plastic transparent glasses. After 5 days of acclimation, plants were transferred to a greenhouse.

REFERENCES

Acciarri Nazzareno, Restaino F., Vitelli G., Perrone D., Zottini M-, Pandolfini T., Spena A. and Rotino G. L. 2002. Genetically modified parthenocarpic eggplants: improved fruit productivity under both greenhouse and open field cultivation BMC Biotechnol.; 2 (1): 4

Ampomah-Dwamena C, Morris B A, Sutherland P, Veit B, Yao J L. 2002. Down-regulation of TM29, a tomato SEPALLATA homolog, causes parthenocarpic fruit development and floral reversion. Plant Physiol.; 130(2):605-17

Barg R, Meir E, Lapushner D, Frankel R, Salts Y. 1990. Differential regulation of a fruit-specific 62 kDa protein in developing parthenocarpic (pat-2/pat-2) and seeded tomato fruits. Physiol Plant 80: 417-424

Bianchi, A. and Soressi, G. P. 1969. Mutanti di pomodoro artificialmente indotti suscettibili di utilizzazione nel miglioramento genetico. Sementi Elette XV 3:2-6

Bowman J., Smyth D., Meyerowitz E. 1989. Genes directing flower development in *Arabidopsis*. The Plant Cell 1: 37-52

Clough S J, Bent A F. 1998. Floral dip: a simplified method for *Agrobacterium*-mediated transformation of *Arabidopsis thaliana*. Plant J. 16(6):735-43.

Coombe, B. G. 1975. The development of fleshy fruits. Ann. Rev. Plant Physiol. 27, 507-528

Chandler, J. L., Z. Viloria and J. W. Grosser. 2000. Acid citrus fruit cultivar improvement via interploid hybridization. Proc. Fla. State Hortic. Soc. 113:124-126.

Deng, X. X., W. W. Guo and X. H. Sun. 1996. Advances in breeding and selection of seedless types of Citrus in China. Acta Hortic. Sin. 23:235-240.

Donzella, G, Spena, A, & Rotino, GL. 2000. Transgenic parthenocarpic eggplants: superior germplasm for increased winter production. Mol Breed, 6:79-86.

Espinoza C., Vega, A., Medina, C., Schlauch, K., Cramer, G. and Arce-Johnson, P. 2006. Analysis of gene expression associated with compatible viral diseases in grapevine cultivars (accepted, Functional and Integrative Genomics).

Ficcadenti, N, Sestili, S, Pandolfini, T, Cirillo, C, Rotino, GL, & Spena, A, 1999. Genetic engineering of parthenocarpic fruit development in tomato. Mol Breed, 5:463-470.

Franks T, He Gang D and Thomas M. 1998. Regeneration of transgenic *Vitis vinifera* L. Sultana plants: genotypic and phenotypic analysis. Molecular Breeding; 4: 321-333.

Gamborg O L, Miller R A, Ojima K. 1968. Nutrient requirements of suspension cultures of soybean root cells. Exp Cell Res. 50: 1515-1518.

García-Martínez J L, Hedden P. 1997. Gibberellins and fruit development. In FA Tomás-Barberán, R J Robins, Eds, Phytochemistry of Fruit and Vegetables. Clarendon Press, Oxford, pp 263-286.

George W L, Scott J W, Splittstoesser W E. 1984. Parthenocarpy in tomato. Hortic Rev 6: 65

Gillaspy G. et al. 1993. Fruits: a developmental perspective. Plant Cell 5:1439-1451

Gibeaut D M, Hulett J, Cramer G R, Seemann J R (1997) Maximal biomass of *Arabidopsis thaliana* using a simple, low-maintenance hydroponic method and favourable environmental conditions. Plant Physiol. 115: 317-319.

Goes da Silva F G, Iandolino A, Al-Kayal F, Bohlmann M C, Cushman M A, Lim H, Ergul A, Figueroa R, Kabuloglu E K, Osborne C, Rowe J, Tattersall E, Leslie A, Xu J, Baek J, Cramer G R, Cushman J C, Cook D R (2005). Characterizing the grape transcriptome. Analysis of expressed sequence tags from multiple *Vitis* species and development of a compendium of gene expression during berry development. Plant Physiol. 139(2): 574-97.

Guo, W. W., X. Deng and H. L. Yi. 2000. Somatic hybrids between navel orange and grapefruit for seedless triploid breeding. Euphytica 116:281-285.

Honma T, Goto K. 2001. Complexes of MADS-box proteins are sufficient to convert leaves into floral organs. Nature 409: 525-529

Ito T. Fromm M., Meyerowitz E. 2002. Plants having seedless fruit. US Patent 20020152495.

Kaufmann K, Melzer R, Theissen G. 2005. MIKC-type MADS-domain proteins: structural modularity, protein interactions and network evolution in land plants. Gene 347(2):183-98.

Kihara, H. 1951. Triploid watermelon. Proc. Am. Soc. Hort. Sci., 58, 217-230.

Kihara, H. 1958. Breeding of seedless fruits. Seiken Ziho, 9, 1-7.

Korneef M., Van Eden J., Hanhart C J. Stam P., Braaksma F J., Feenstra W J. 1983. Linkage map of *Arabidopsis thaliana*. J. Hered. 74: 265-272.

Liu, Y-G and Huang, N. 1998. Efficient amplification of insert end sequences from bacterial artificial chromosome clones by thermal asymmetric interlaced PCR. Plant Mol. Biol. Report. 16: 175-181.

López-Pérez A J., Carreño J., Martínez-Cutillas A., Dabauza M. 2005. High embryogenic ability and plant regeneration of table grapevine cultivars. *Vitis* 44(2):79-85.

Lukyanenko A. N., Parthenocarpy in tomato. In: G. Kalloo, Ed. 1991. Monographs on Theoretical and Applied Genetics: Genetics Improvement of Tomato, Springer-Verlag, pp. 167-178.

Mezzetti B., Lucia Landi, Tiziana Pandolfini and Angelo Spena. 2004. The defH9-iaaM auxin-synthesizing gene increases plant fecundity and fruit production in strawberry and raspberry. BMC Biotechnol. 4 (1): 4

Mezzetti, B, Landi, L, Scortichini, L, Rebori, A, Spena, A, and Pandolfini, T. 2002: Genetic engineering of parthenocarpic fruit development in strawberry. Proc. 4th ISHS Strawberry symposium, Tampere (Finland) 9-14 Jul. 2000. Acta Hortic, 567:101-104.

Murashige T. and Skoog F. 1962. A revised medium for rapid growth and bioassays with tobacco tissue culture. Physiol Plant. 15:473-497.

Nitsch J., Hulme A C. 1970. Hormonal factors in growth development. In: A. C. Hulme, Editor, The Biochemistry of Fruits and their Products (Vol. 2), Academic Press, pp. 427-472

Nitsch J P and Nitsch C. 1969. Haploid plants from pollen grains. Science. 163:85-87.

Nothman, J & Koller, D. 1975. Effects of growth regulators on fruit and seed development in eggplant (*S. melongena* L.). J Hort Sci, 50:23-27

Pandolfini, T, Rotino, G L, Camerini, S, Defez, R, & Spena, A. 2002. Optimisation of transgene action at the post-transcriptional level: high quality parthenocarpic fruits in industrial tomatoes. BMC Biotechnology 2:1.

Pelaz S, Tapia-Lopez R, Alvarez-Buylla E R, Yanofsky M F. 2001. Conversion of leaves into petals in *Arabidopsis*. Curr Biol. 11 (3):182-4.

Pelaz S., G. S. Ditta, E. Baumann, E. Wisman and M. F. Yanofsky. 2000. B and C floral organ identity functions require SEPALLATA MADS-box genes. Nature 405. 200-203.

Philouze J. 1983. Parthenocarpie naturelle chez la tomate. I. Revue bibliographique. Agronomie 3: 311-320

Pnueli L, Hareven D, Broday L, Hurwitz C, Lifschitz E. 1994. The TM5 MADS Box Gene Mediates Organ Differentiation in the Three Inner Whorls of Tomato Flowers. Plant Cell. (2):175-186.

Porebski, S. et al. 1997. Modification of a CTAB ADN extraction protocol for plants containing high polysaccharide and polyphenol components. Plant Mol. Biol. Report. 15, 1:8-15.

Romano, D & Leonardi, C. 1994. The responses of tomato and eggplant to different minimum air temperature. Acta Hort. 366:57-66

Rotino, G L, Sommer H, Saedler H, Spena A. 1996. Methods for producing parthenocarpic or female sterile transgenic plants and methods for enhancing fruit setting and development. EPO patent N EPO 96120645.5.

Rotino, G L, Perri, E, Zottini, M, Sommer, H, & Spena, A. 1997. Genetic engineering of parthenocarpic plants. Nat Biotechnol, 15:1398-1401.

Schwabe, W. W. and Mills, J. J. 1981. Hormones and parthenocarpic fruit set: A literature survey. Hortic. Abst. 51, 661-699.

Shaefer S., Gasic K., Cammue B., Broekaert W., van Damme E., Peumans W., Korban S. 2005. Enhanced resistance to early blight in transgenic tomato lines expressing heterologous plant defense genes. Planta 222(5): 858-866.

Soressi G P, Salamini F. 1975. A mono-Mendelian gene inducing parthenocarpic fruits. Rep Tomato Genet Coop 25:22.

Sugiyama K. and Morishita M. 2002. New Method of Producing Diploid Seedless Watermelon Fruit JARQ 36 (3), 177-182

Szechtman A D, Salts Y, Carmi N, Shabtai S, Pilowsky M, Barg R. 1997. Seedless fruit setting in response to NAM treatment of transgenic tomato expressing the iaaH gene specifically in the ovary. Acta Hort 447:597-698

Terada, J. & Masuda, K. 1943. Parthenocarpy of triploid watermelon. Agric. Hort., 18, 15-16.

Vicient C M, Delseny M. 1999. Isolation of total ARN from *Arabidopsis thaliana* seeds. Anal Biochem. 268 (2):412-3.

Vliet G. 1998. Seedless tomato and method for producing seedless tomato, hybrid tomato plants capable of producing said seedless tomatoes and cultivation material therefore, and food products obtained form said seedless tomatoes. US patent 20020010953 WO 98/24301.

Vionet O. 2003. ARN silencing bridging the gaps in wheat extracts. Trends in Plant Science (8)7:307-309.

Watanabe, S. et al. 2001. Effect of growing season on formation of empty seed in seedless watermelon fruits produced by soft-X-irradiated pollen. In Abstract 2nd International Symposium on Cucurbits, 65.

Yao J, Dong Y, Morris B A. 2001. Parthenocarpic apple fruit production conferred by transposon insertion mutations in a MADS-box transcription factor. Proc. Natl. Acad. Sci USA. 98(3):1306-11.

SEQ. ID. No. 1
ATGGGGAGAGGGAAGATTGAGATCAAGAGGATCGAGAACTCAAGCAACAG
GCAGGTGACCTACTCAAAGAGGAGAAATGGGATCATGAAGAAGGCCAAGG
AGATCACTGTTCTCTGCGATGCTCATGTCTCTCTTGTTATCTTTGCTAGC
TCTGGAAAGATGCACGAGTACTGTAGCCCTTCTACAACGTATGGAGTTCT
TTTTTTTCCTTCCTGGATATTTGTTTCTTTGATTTAATCCTTCTGGGTTT
TCTTTGTTTTTCTAACTCCCTCTTTTCCTGGGTTTTTTCCCATGTGGGTG
CTTTCATCTGGTGAAGGTTGATTGATATCTTGGATAGGTATCACAAGCAG
TCTGGGAAGAGGCTCTGGGATGCAAAACATGAAGTGGGTTTGATTCTTTG
ATATATTTTCCCCACTCTTCCTGTCATTTTTTTATTTGTAAAAGCATCT
GGAGTTTCTTGTTTGTCCCAGTGGAAAATGACATACTTCTTTTGCTAAAA
ACATGTTAAGGAACACGAAATATGAATTCTATGAACAGATCTCTTCATGA
GCATGCCTCTTGTAAATGTCTGTTAAGATGTACTAACTGTTAAGGGAAAA
ACTCAGAAAATCTCAGCAATGAATTGGATAGGATCAAAAGGAGAATGAT
AGCATGCAGATTGAACTCAGGTAGATAGATCTCTCCTTCTCTTTAGNTTC
ATCTCTCTCTCTCTCTTTTACTTACATGTATGTTACAGGAGATAGATCTC
TCCTTCTCNTAGTTCATCTCTCTCTCTCTCTTTTATTACATGNTGTAAAG
GCACCTGAAGGGGGAGGATATCTCATCTCTGCACCACAAAGAACTCATGG
CCATTGAGGATGCCCTTGAGATTGGCCTTGCAAGTGTTCGCAACAAACAG
GCAAGTTCTCTCACACTGTAATATTTTACATACACATTGGTTGAAGTTCT
GAAGAGATAATATCCCAAATAACTTCTGATCTTCCCCCTTTGTGACAGGC
AAGTTCTCTCACACTGTAATATTTTACATACACATTGGTTGAAGTTCTGA
AGAGATAATATCCCAAATAACTTCTGATCTTCTCCCTTNGTGACAGATGG
AATTCTACAAGATGGTCAAGAAAAATTATTTTACATACACATTGGTTGAA
GTTCTGAAGAGATAATATCCCAAATAACTTCTGATCTTCCCCCTTTGTGA
CAGATGGAATTCTACAAGATGGTCAAGAAAAATGTATGTATAGAGTCTAT
AACCAGACAAACAATTATCCCATGGAAGATCTTAAATTCTTGCCTTTGTT
TTGATGGGGTTGTCATTGGCTTGTTGGCCTATATTTGTCTCTATGGTTGC
TTCTTTGATCTACAAATACCAAAGAGAGGGAGAGAGAAAAAAAATTTCAA
TTTTGTTCATGTTCCTAAGTAGGTTAAAGATTTGCTAGTTGCCTAACTTC
TTTATTTTTGGGTGAACATTCTCAGCAACGAATCCTGGAGGAGGAGAACA
AGCACCTCAATTACATCGTGGTATGTTATTATCACAATACATTATTAACA
CACTTAACACATTCGTGTATATGGATAAAAAAGGTGTAGATGTACATGG

AAGGAAATGTTCGTAGTTTCTTCTTTCTATCGCATGGTTCATCTATATAT

TCTATTCATGGTCATGTCACCGGAAAATGTTCTAGCTAGAACACCGTCTA

CTAGTTTTGAACTTCATATTAATAATTGTTCATCCAACAAAGAAGCTGGC

CGGGCAGGACTCCCTGAATTGTTTTGTTTATTGTCTGCAGCACCACCAGG

GTATGCCCATGGAGGCGGGCAATGTGAGAGAGGTGGAAAGTGGATATCAT

CAGAGAGCTGTGAGGGACTACAATCCCCAGATGCCTTTCGCCTTCCGGGT

GCAGCCAATTCAGCCAAACTTACAGGAGAGGATATAACTCTCTTAGCTAT

ATATATAGTTTGTGCTTTAATTAAGAAGGATACATTCCAGACTTGCAATA

GGGTTTGTTGTAGAGGTGATCTTATTCTCCTTCAGCCATTACCCTCAAAA

TCTATAATAATTAAGGTGTGTGATCTTGGTTTGTGAAACTTTATATATAT

ATATATATATATCTTTGAATGCTTGCTGACTACC

SEQ. ID. No. 2
ATGGGGAGAGGGAAGATTGAGATCAAGAGGATCGAGAACTCAAGCAACAGG

CAGGTGACCTACTCAAAGAGGAGAAATGGGATCATGAAGAAGGCCAAGGAG

ATCACTGTTCTCTGCGATGCTCATGTCTCTCTTGTTATCTTTGCTAGCTCT

GGAAAGATGCACGAGTACTGTAGCCCTTCTACAACGTTGATTGATATCTTG

GATAGGTATCACAAGCAGTCTGGGAAGAGGCTCTGGGATGCAAAACATGAA

AATCTCAGCAATGAATTGGATAGGATCAAAAAGGAGAATGATAGCATGCAG

ATTGAACTCAGGCACCTGAAGGGGGAGGATATCTCATCTCTGCACCACAAA

GAACTCATGGCCATTGAGGATGCCCTTGAGATTGGCCTTGCAAGTGTTCGC

AACAAACAGATGGAATTCTACAAGATGGTCAAGAAAAATCAACGAATCCTG

GAGGAGGAGAACAAGCACCTCAATTACATCGTGCACCACCAGGGTATGCCC

ATGGAGGCGGGCAATGTGAGAGAGGTGGAAAGTGGATATCATCAGAGAGCT

GTGAGGGACTACAATCCCCAGATGCCTTTCGCCTTCCGGGTGCAGCCAATT

CAGCCAAACTTACAGGAGAGGATATAA

SEQ. ID. No. 3
CTCTCTTAGCTATATATATAGTTTGTGCTTTAATTAAGAAGGATACATTCC

AGACTTGCAATAGGGTTTGTTGTAGAGGTGATCTTATTCTCCTTCAGCCAT

TCCCTCC

SEQ. ID. No. 4
TAGTGTAGTAGCAGNAGAGCAGATAATGGCAGTTTGGCTTGGCTATGTCAA

CAACCCATAAACAAGTCGTCCATTCTGTGGCTCTGGAAAGTTCATTATCCC

CCAACTTATATTGGAATGCTCCTCCATTACTTTCCTTTCTTTTTCTTTTTC

ACTGCTTTTAGTCCTTTATATCATCTCTCCAGGAAGAGGAGGAAGAAGAGA

AAGAGAGAAGAAGAGGGTTTGGTTTGGAGAGAG

SEQ. ID. No. 5
MGRGKIEIKRIENSSNRQVTYSKRRNGIMKKAKEITVLCDAHVSLVIFASS

GKMHEYCSPSTTLIDILDRYHKQSGKRLWDAKHENLSNELDRIKKENDSMQ

IELRHLKGEDISSLHHKELMAIEDALEIGLASVRNKQMEFYKMVKKNQRIL

EEENKHLNYIVHHQGMPMEAGNVREVESGYHQRAVRDYNPQMPFAFRVQPI

QPNLQERI

SEQ. ID. No.6
ATGGGGAGAGGGAAGATTGAGATAAAGAGAATAGAAAACACAAACAACAGG

CAAGTAACTTATTCAAAAAGAAGAAATGGTATAATAAAGAAAGCTAAAGAA

ATTACTGTTCTTTGTGAAGCTAAGGTTTCACTTATAATCTTTGCTAGTTCT

GGAAAGATGCATGAATATTGTAGCCCTTCTACTACGATAAGTGATATGTTG

GATGGTTATCAAAAAGCTTCTGGGAGGAGACTATGGGATGCTAAGCATGAG

AATTTGAGTAATGAAATTGATAGAATCAAGAAAGAGAATGACAGTATGCAG

GTTAAGCTCAGGCACCTCAAAGGAGAAGATATCAATCAACTTACCCATAAA

GAGCTTATAATTATGGAAGAAGCCTTACAAAATGGACTTTCTAGTATCAGT

GCCAAGCAGTCTGAAATCTTGAGATGGTCAGGAAAAATGATCAAATTCTGG

AGGAGGAAAATAAGCAACTTCAATATGCTTTGCACCAAAAGGAGATGGGAG

CCATTGGTGGAAGTGGAAATATGAGAGGAATTCATGAAGAAGGTATCATCA

AAGAGAAAGGGATTATGAGTACCAAATGCCATTTGGCCTACGAGTCCAGCC

AATGCAGCCTCATCTACATGAAAGAATGTAA

SEQ. ID. No. 7
MGRGKIEIKRIENTNNRQVTYSKRRNGIIKKAKEITVLCEAKVSLIIFASS

GKMHEYCSPSTTISDMLDGYQKASGRRLWDAKHENLSNEIDRIKKENDSMQ

VKLRHLKGEDINQLTHKELIIMEEALQNGLSSISAKQSEILRMVRKNDQIL

EEENKQLQYALHQKEMGAIGGSGNMRGIHEEVYHQRERDYEYQMPFGLRVQ

PMQPNLHERM

What is claimed is:

1. A method to produce sterile male flowers and parthenocarpic fruits by genetic silencing wherein said method comprises the steps of:

a) making a genetic silencing construct comprising SEQ ID NO: 1 or SEQ ID NO:2;

b) incorporating the construct into *Agrobacterium tumefaciens*;

c) transforming target plants with *Agrobacterium tumefaciens* modified with the silencing construct and selecting transformed plants;

d) assessing the absence of *Agrobacterium* contamination and corroborating transgenic plants by transgene amplification.

2. The method to produce sterile male flowers and parthenocarpic fruits according to claim 1, wherein the construct comprises an expression vector comprising a regulatory promoter sequence.

3. The method to produce sterile male flowers and parthenocarpic fruits according to claim 2, wherein the promoter sequence can have tissue specific, inducible or strong constitutive expression.

4. The method to produce sterile male flowers and parthenocarpic fruits according to claim 2, wherein the expression vector is incorporated into *Agrobacterium tumefaciens*-like bacteria.

5. The method to produce sterile male flowers and parthenocarpic fruits according to claim 1, wherein the genetic silencing construct silences the Pistillata gene function in *Vitus vinifera* transgenic plants.

6. The method to produce sterile male flowers and parthenocarpic fruits according to claim 1, wherein in step (c) the transformation of target plants with *Agrobacterium tumefaciens* modified with the silencing vector is made by immersing explants from the target plant in a bacterial suspension that contains the modified *Agrobacterium tumefaciens*.

7. The method to produce sterile male flowers and parthenocarpic fruits according to claim 1, wherein in step (d) transgenic plants are identified by transgene amplification by a PCR technique.

8. The method to produce sterile male flowers and parthenocarpic fruits according to claim 1, wherein the target species is *Vitis vinifera* cv. Cabernet Sauvignon.

9. A genetic silencing vector to produce sterile male flowers and parthenocarpic fruits comprising SEQ ID NO:1.

10. A genetic silencing vector to produce sterile male flowers and parthenocarpic fruits comprising SEQ ID NO:2.

* * * * *